United States Patent [19]
Papenfuhs

[11] Patent Number: 4,727,154
[45] Date of Patent: Feb. 23, 1988

[54] PROCESS FOR THE PREPARATION OF 2-SUBSTITUTED BENZOTHIAZOLES

[75] Inventor: Theodor Papenfuhs, Frankfurt am Main, Fed. Rep. of Germany

[73] Assignee: Hoechst Aktiengesellschaft, Frankfurt am Main

[21] Appl. No.: 891,524

[22] Filed: Jul. 31, 1986

[30] Foreign Application Priority Data

Aug. 5, 1985 [DE] Fed. Rep. of Germany ....... 3528032

[51] Int. Cl.$^4$ ........................................... C07D 277/64
[52] U.S. Cl. .................................. 548/150; 548/152; 548/178; 548/179; 548/180
[58] Field of Search ............... 548/150, 152, 178, 179, 548/180

[56] References Cited

U.S. PATENT DOCUMENTS 2,055,609  9/1936  Lubs et al. ............................ 548/150
4,370,483  1/1983  Papenfuhs ............................ 548/165
4,429,134  1/1984  Papenfuhs ............................ 548/150
4,556,411 12/1985  Baum et al. ........................... 548/150

FOREIGN PATENT DOCUMENTS 0039483 11/1984  European Pat. Off.
2801991  8/1980  Fed. Rep. of Germany.
3337859  7/1984  Fed. Rep. of Germany ...... 548/152

Primary Examiner—Mary E. Ceperley

[57] ABSTRACT

Process for the preparation of benzothiazoles of the formula (1)

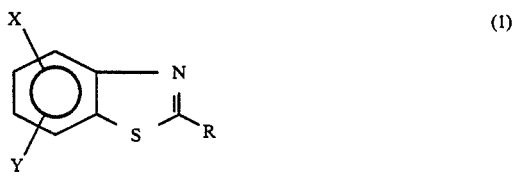

wherein R denotes an alkyl$_{C1-C6}$ or an a kenyl$_{C2-C6}$ group which can be substituted by alkoxy$_{C1-C4}$, acyl, phenyl, chlorophenyl, bromophenyl, alkyl$_{C1-C4}$phenyl, alkoxy$_{C1-C4}$-phenyl or nitrophenyl groups or halogen atoms, or denotes a phenyl group which can be substituted by alkyl$_{C1-C4}$, alkoxy$_{C1-C4}$, carboxyl-, —COO-alkyl$_{C1-C4}$, cyano or nitro or halogen atoms, and X and Y each denote a hydrogen or halogen atom or an alkyl$_{C1-C4}$, alkoxy$_{C1-C4}$ or nitro group, or together denote a fused benzene ring, wherein the salts of the corresponding 2-mercaptophenylureas of the formula (5)

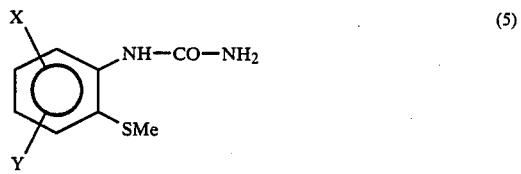

in which X and Y have the stated meansings and Me denotes an alkali metal atom or the equivalent amount of an alkaline earth metal atom, which salts are obtainable as intermediate compounds in a known manner by reacting 2-aminobenzothiazoles of the general formula (4)

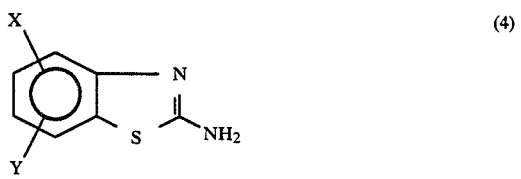

in which X and Y have the abovementioned meanings, with alkali metal or alkaline earth metal hydroxides in an anhydrous or virtually anhydrous solvent, are treated, in the isolated form or in suspension in the ring-opening mixture, with an acylating agent of the formula (3)

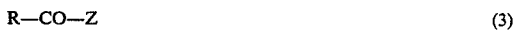

R—CO—Z                (3)

in which R has the abovementioned meaning and Z represents a halogen atom or the group

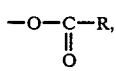

wherein R has the stated meaning, or with diketene at temperatures from 0° C. to 200° C.

5 Claims, No Drawings

PROCESS FOR THE PREPARATION OF 2-SUBSTITUTED BENZOTHIAZOLES

The invention relates to a process for the preparation of 2-substituted benzothiazoles which are valuable intermediates for the preparation of dyes, crop protection agents and pharmaceuticals, the said process constituting an improvement in terms of industrial hygiene and waste water disposal and giving a higher yield.

2-Substituted benzothiazoles of the general formula (1),

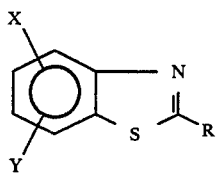
(1)

in which R denotes an alkyl$_{C_1-C_6}$ or alkenyl$_{C_2-C_6}$ group which can be substituted by alkoxy$_{C_1-C_4}$ groups, acyl groups, such as, for example, acetyl or benzoyl groups, a phenyl, chlorophenyl, bromophenyl, alkyl$_{C_1-C_4}$ phenyl group, such as, for example, methylphenyl or ethylphenyl groups, an alkoxy$_{C_1-C_4}$ phenyl group, such as, for example, methoxyphenyl or ethoxyphenyl groups, or a nitrophenyl group, or halogen atoms, such as, for example, chlorine or bromine atoms, or denotes a phenyl group which can be substituted by alkyl$_{C_1-C_4}$, alkoxy$_{C_1-C_4}$, carboxyl, —COO-alkyl, cyano or nitro groups or by halogen atoms, such as, for example, chlorine or bromine atoms, and X and Y each denote a hydrogen or halogen atom, for example a chlorine or bromine atom, or an alkyl$_{C_1-C_4}$, alkoxy$_{C_1-C_4}$ or nitro group, or together denote a fused benzene ring, have been produced to date industrially by reacting o-aminothiophenols of the general formula (2)

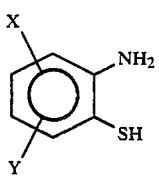
(2)

in which X and Y have the abovementioned meanings, with compounds of the general formula (3) (carboxylic acids, carboxylic acid halides or carboxylic anhydrides)

R—CO—Z (3)

in which R has the abovementioned meaning and Z denotes a halogen atom, for example a chlorine or bromine atom, a hydroxyl group or the group

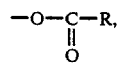

wherein R has the meanings stated further above, according to the equation

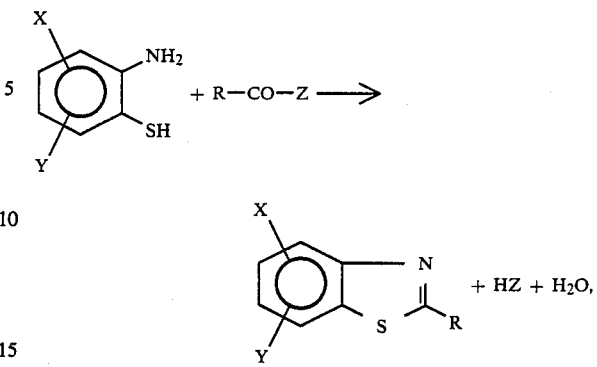

or with special carboxylic anhydrides, such as, for example, diketenes.

The o-aminothiophenols used as starting materials are prepared from corresponding nitro precursors, and in individual cases even by total alkaline hydrolysis of 2-aminobenzothiazoles or benzothiazthionium halides.

All known industrial syntheses of 2-substituted benzothiazoles of the stated formula (1) therefore take place via free aryl mercaptans, with the result that considerable problems are encountered with respect to industrial hygiene and waste water disposal.

Furthermore, from a chemical point of view, for the reason below, there was a need for a more effective process for the industrial preparation of the compounds of the formula (1):

The starting materials of the stated formula (2), being free mercaptans, are very sensitive to oxidation and inevitably result in a reduction in yield through conversion to 2-aminophenyl disulfides.

It has now been found, surprisingly, that 2-substituted benzothiazoles of the general formula (1) stated further above can be prepared by a method which completely avoids the abovementioned disadvantages associated with the known preparation processes, and in which the salts of the corresponding 2-mercaptophenylureas of the general formula (5)

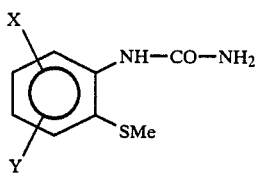
(5)

in which X and Y have the stated meanings and Me denotes an alkali metal atom or the equivalent amount of an alkaline earth metal atom, which salts are obtainable as intermediate compounds in high yields, in a known manner [European Pat. No. 0,039,483 (U.S. Pat. No. 4,370,483)] by reacting 2-aminobenzothiazoles of the general formula (4)

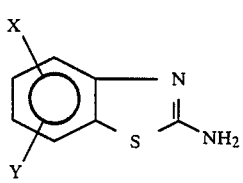
(4)

in which X and Y have the abovementioned meanings, with alkali metal or alkaline earth metal hydroxides in an anhydrous or virtually anhydrous solvent, such as ethanol, isobutanol, 1,2-dihydroxypropane or 1,3-dihydroxypropane, preferably ethylene glycol, glycerol, ethylene glycol monomethyl ether or ethylene glycol monoethyl ether, are treated, in the isolated form or in suspension in the ring-opening mixture, with an acylating agent of the general formula (3)

R—CO—Z          (3)

in which R and Z have the meanings mentioned further above, or with a special carboxylic anhydride, such as, for example, diketene, at temperatures of 0° C. to 200° C., preferably 40° C. to 160° C.

The S-acylmercaptophenylureas of the formula (6) which are formed as intermediates in this process are stable to hydrolysis only in exceptional cases but can be isolated under completely anhydrous conditions. As a rule, they are hydrolyzed in a short time under the reaction conditions by the water present in the reaction mixture or added subsequently, with elimination of ammonia and carbon dioxide, to give S-acyl-o-aminothiophenols of the formula (7), which are cyclized, particularly rapidly at elevated temperatures, with elimination of water to give the end compounds of the stated general formula (1), according to the following equation:

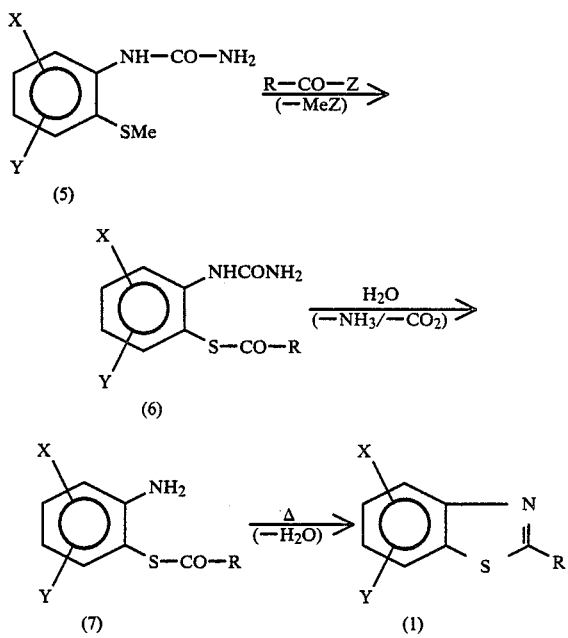

Thus, in the process according to the invention, the 2-aminobenzothiazoles of the stated formula (4), which are readily obtainable industrially according to, for example, German Pat. No. 2,801,991, can be converted in high yield and purity to 2-substituted benzothiazoles of the stated formula (1) in a one-pot reaction by reaction with an alkali metal hydroxide or alkaline earth metal hydroxide and then with an acylating agent of the stated formula (3). The process according to the invention avoids the use of free thiophenols and therefore does not present any ecological problems or problems with regard to industrial hygiene. Consequently, and in conjunction with the higher yields obtainable, the process according to the invention constitutes substantial technical progress.

Furthermore, it is surprising that, in the process according to the invention, no marked formation of byproducts is observed. It was in fact to be expected that, in the acylation step (in the presence of water), acid liberated, if only in traces and in a localized manner, would permit the acid-catalyzed cyclization of the 2-mercaptophenylurea to the corresponding 2-hydroxybenzothiazole according to European Pat. No. 0,039,483, the said cyclization taking place very readily, and consequently 2-substituted benzothiazoles of the stated formula (1) contaminated by 2-hydroxybenzothiazole would result.

The fact that these expected side reactions occur in no more than traces in the process according to the invention, and a reaction proceeding in virtually only one way therefore leads to the desired end products of the formula (1), was not foreseeable and appears extremely surprising in view of the fact that the reaction takes place in a complex manner in a plurality of synthesis steps.

The process according to the invention is carried out specifically as follows: an acylating agent of the general formula (3), for example a carboxylic acid or its halide or anhydride, or a special carboxylic anhydride, such as, for example, diketene, is added at temperatures of 0°–200° C., preferably 40°–160° C., in at least a molar amount, preferably in excess of 5 to 25%, in the course of 0 to 5, preferably 0.5 to 2, hours to the 2-mercaptophenylurea salt of the general formula (5), as an isolated solid or in the form of the aqueous solution (or, if appropriate, suspension) resulting from the dilution of the ring-opening mixture with water, the said salt being obtainable, for example, according to European Pat. No. 0,039,483, and the 2-substituted benzothiazole formed is separated off from the reaction mixture by phase separation, filtration or extraction and subsequently free from the adhering water or extracting agent.

It is of course also possible to start from free 2-mercaptophenylurea, which can be prepared according to European Pat. No. 0,039,483 and has been isolated, to suspend this in water and, if appropriate, then to neutralize it with a molar amount of an alkali metal or alkaline earth metal hydroxide or carbonate to give the abovementioned salt of the formula (5), and to use this in the process of the invention. Because of the problems associated with free mercaptans as described at the outset, this is not a preferred variant.

Particularly preferred, on the other hand, is the following variant, in which a starting mixture prepared from an isolated 2-mercaptophenylurea salt (formula (5); cf. European Pat. No. 0,039,483, Examples 6–10) and a solvent which is inert to the acylating agent of the formula (3) or, for example, to the diketene under the reaction conditions (toluene, xylenes, chlorobenzene, chlorotoluenes, petroleum ether, and chloroaliphatics), or an isolated 2-mercaptophenylurea salt in the absence of a solvent, is reacted with the acylating agent of the formula (3) or, for example, with the diketene at temperatures of 0°–200° C., preferably 50° to 160° C., in at least a molar amount, preferably in an excess of 5 to 50%, or, in the absence of a solvent, with, if appropriate, a substantially larger excess, in the course of 1 to 10, preferably 2 to 6, hours, if appropriate under pressure. To work up the mixture, the end product of the formula (1) is isolated by filtration, washing out the solvent and the resulting salt with water and drying, or, particularly in the case of liquid or low-melting end products, or end products which are too soluble in the solvent, the said end products, if appropriate after being filtered off from the salt formed, are concentrated by distillation and then obtained in pure form by filtration, washing and drying or, particularly advantageously, by fractionation, preferably in a vacuum of 0.1 to 100 mm Hg.

The examples which follow are intended to illustrate the process according to the invention in more detail without restricting it. The parts stated are parts by weight.

EXAMPLE 1

70 parts of acetic anhydride are added in the course of 15 minutes at 25° to 30° C., while stirring, to the solution of the sodium salt of 6-methyl-2-mercaptophenylurea, which solution is obtained according to Example 3 of European Pat. No. 0,039,483 by reacting 82 parts of 4-methyl-2-aminobenzothiazole with 50 parts of sodium hydroxide and has been clarified with carbon. The reaction is then continued for 2 hours.

The mixture is then heated to the reflux temperature, kept under reflux for 1 hour and cooled to 0° C. During this procedure, the 2,4-dimethylbenzothiazole of the formula

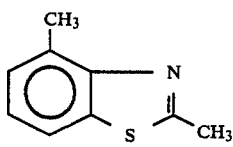

which initially separates out as an oil, forms granules, which are filtered off under suction, washed neutral with water and dried in vacuo at room temperature. 75 parts of product of melting point 33.5° C. are obtained; this corresponds to a yield of 92.0% of theory, based on 4-methyl-2-aminobenzothiazole employed.

The 2,4-dimethylbenzothiazole dissolves in dilute hydrochloric acid to give a clear solution, and the gas chromatogram (measured against an internal standard) shows that it is 99.2% pure. The purity can also be determined by potentiometric titration with perchloric acid in glacial acetic acid, and is found by this method to be 98.9%.

If the acetic anhydride is replaced by aliquot amounts of acetyl chloride, and the procedure is otherwise carried out in the manner stated, a comparable result is obtained.

EXAMPLE 2

The water-moist 2-mercaptophenylurea obtained according to European Pat. No. 0,039,483, Example 1, paragraph 1, by reacting 150 parts of 2-aminobenzothiazole with 150 parts of sodium hydroxide and working up the mixture with water, or an appropriate amount of the sodium or potassium salt of the said 2-mercaptophenylurea, is dissolved in 500 parts of 50% strength acetic acid, and 118 parts of diketene are then added dropwise in the course of 2 hours at 45° to 50° C. Stirring is continued for 1 hour, after which the mixture is heated to the reflux temperature and kept at a temperature of 95° C.-100° C. for 2 hours. It is then cooled to room temperature, and the precipitated 2-acetonylbenzothiazole of the formula

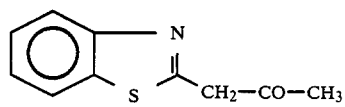

is isolated by filtration and dried in vacuo at 60° C.-80° C. 151.7 parts of a product of melting point 118° C.-119° C. are obtained; this corresponds to a yield of 79.4%, based on 2-aminobenzothiazole employed.

The product is pure according to chromatography, and is shown by potentiometric titration with perchloric acid in glacial acetic acid to have a purity of 98.4%.

EXAMPLE 3

85 parts of the sodium salt of 2-mercaptophenylurea (prepared according to Example 1 of European Pat. No. 0,039,483, by reacting 2-aminobenzothiazole with sodium hydroxide in ethylene glycol at 140° C., then filtering the reaction mixture and drying the resulting filter cake in vacuo at 100° C.) or suspended in 400 parts of chlorobenzene.

69.5 parts of phenylacetyl chloride are added in the course of 1 hour at 60° C.-70° C., while stirring, after which the mixture is heated to 130° C. (reflux) and kept at this temperature for 2 hours. Thereafter, the solution is clarified by removing the precipitated sodium chloride, about 250 parts of chlorobenzene are distilled off in vacuo from the filtrate, and the remaining bottom product is cooled to room temperature. The precipitated 2-benzylbenzothiazole of the formula

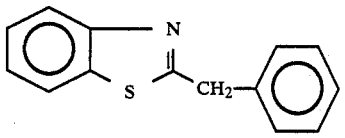

is filtered off under suction, washed with a small amount of chlorobenzene and dried in vacuo at 60° C.-70° C.

102 parts of a product of melting point 110° C.-111° C. are obtained; this corresponds to a yield of 90.7% of theory, based on sodium salt employed. The purity determined by potentiometric titration (HClO₄ in glacial acetic acid) is 99.1%. No impurities are detectable by chromatography.

EXAMPLES 4-10

If, in Example 3, the phenylacetyl chloride is replaced by aliquot parts of the acylating agents listed in Table 1 below (corresponding to the stated general formula (3), and the procedure is carried out in the manner stated, in the case of liquid end products distillative working-up being carried out by fractionating the chlorobenzene filtrate after the latter has been freed from the salt, the 2-substituted benzothiazoles (corresponding to the stated general formula (1) in which X and Y=H) shown in Table 1 are obtained, these compounds having the stated melting points or boiling points, yields, and purities (P) determined by potentiometric titration (HClO₄ in glacial acetic acid):

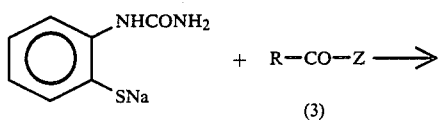
+ R—CO—Z ⟶
(3)

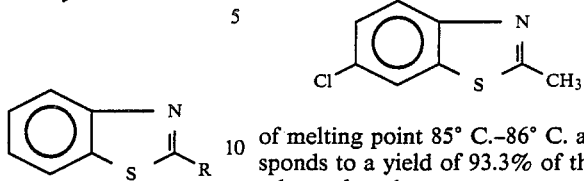

of melting point 85° C.–86° C. are obtained; this corresponds to a yield of 93.3% of theory, based on sodium salt employed.

TABLE 1

| Example | R | Z | End compound (1) R | M.p. °C. | B.p. (mmHg) °C. | Yield | P |
|---|---|---|---|---|---|---|---|
| 4 | $C_2H_5$ | $OCOC_2H_5$ | $C_2H_5$ | | b.p.$_7$: 115° | 88.4% | 98.7% |
| 5 | $CH_2Cl$ | Cl | $CH_2Cl$ | | b.p.$_{15}$: 145° | 86.9% | 99.1% |
| 6 | n-$C_4H_9$ | Br | n-$C_4H_9$ | | b.p.$_7$: 132° | 92.4% | 97.5% |
| 7 | t-$C_4H_9$ | Cl | t-$C_4H_9$ | | b.p.$_{16}$: 138° | 90.4% | 98.0% |
| 8 | $CH_2$—⟨phenyl⟩—$NO_2$ | Cl | $CH_2$—⟨phenyl⟩—$NO_2$ | 114° | — | 94.3% | 97.8% |
| 9 | CH=CH—⟨phenyl⟩ | Cl | CH=CH—⟨phenyl⟩ | 110–111° | — | 92.9% | 98.9% |
| 10 | $CH_2$—$CH_2$—⟨phenyl⟩ | Cl | $CH_2$—$CH_2$—⟨phenyl⟩ | 62° | — | 88.7% | 98.9% |

EXAMPLE 11

112.25 parts of the sodium salt of 4-chloro-2-mercaptophenylurea, which salt is obtainable according to Example 6 of European Pat. No. 0,039,483, are suspended in 450 parts of glacial acetic acid in an autoclave. The pressure vessel is closed and heated slowly to 150° C.–160° C. in the course of 2 hours, a pressure of about 5 bar being established. The water formed is discharged continuously via a pressure release valve. The reaction is complete after 5 hours. The autoclave is cooled to room temperature and opened, the reaction mixture is allowed to run into 1000 parts of water, and the precipitated 6-chloro-2-methylbenzothiazole is isolated by filtration, washed neutral and dried in vacuo at 40° C. 85.6 parts of a product of the formula The compound is pure according to chromatography and is shown by potentiometric titration with $HClO_4$ in glacial acetic acid to have a purity of 98.9%.

EXAMPLES 12–21

If, in Example 11, the sodium salt of 4-chloro-2-mercaptophenylurea is replaced by aliquot amounts of a salt of the general formula (8) and the procedure is otherwise carried out in the stated manner, with subsequent distillative working up of the autoclave contents by fractionation in the case of liquid end products, the 2-methylbenzothiazoles of the formula (9) which are listed in Table 2 are obtained in the yields and purities stated in the table (the purities being determined by potentiometric titration with $HClO_4$ in glacial acetic acid) and with the melting points or boiling points recorded there:

TABLE 2

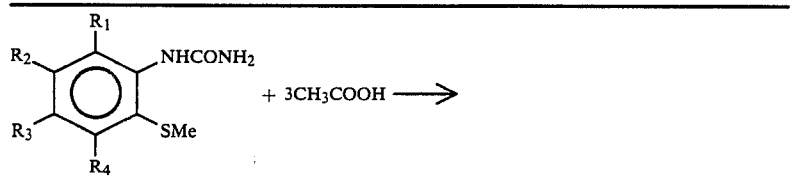

(8)

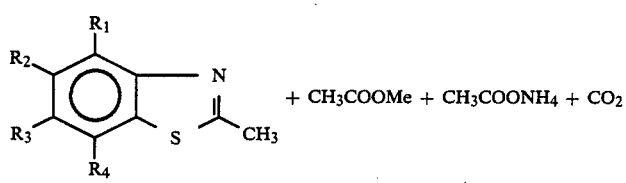

(9)

| | | | | | | End compound (9) | | | |
|---|---|---|---|---|---|---|---|---|---|
| Example | Me | $R_1$ | $R_2$ | $R_3$ | $R_4$ | M.p. °C. | B.p. (mmHg) °C. | Yield | P |
| 12 | Na | H | H | H | H | — | b.p.$_{15}$: 115° | 86.4% | 99.4% |
| 13 | Mg/2 | Cl | H | H | H | 54° | — | 89.7% | 99.2% |
| 14 | Na | H | F | H | H | — | b.p.$_7$: 112° | 85.9% | 99.2% |
| 15 | Na | H | H | $NO_2$ | H | 174° | — | 92.8% | 98.8% |
| 16 | K | H | H | $OCH_3$ | H | — | b.p.$_{25}$: 176° | 81.8% | 99.0% |
| 17 | K | H | H | $OC_2H_5$ | H | 56° | — | 84.0% | 98.3% |
| 18 | Na | H | H | H | $CH_3$ | 31° | — | 86.9% | 96.1% |
| 19 | Na | Br | H | Br | H | 121° | — | 94.1% | 98.4% |
| 20 | Na | $CH_3$ | H | Cl | H | 78° | — | 93.8% | 98.0% |
| 21 | Na | benzo | | H | H | 95° | — | 90.8% | 98.2% |

EXAMPLE 22

112.25 parts of the dry sodium salt of 4-chloro-2-mercaptophenylurea, which salt is obtainable according to Example 6 of European Pat. No. 0,039,483, are suspended in 350 parts of o-dichlorobenzene. 90 parts of phenylacetyl chloride are added dropwise at 70° C.-80° C. in the course of 30 minutes, while stirring, and the mixture is heated to the boil (about 165° C.) and kept at this temperature for 4 hours. It is then cooled to 80° C.-90° C., the solvent is distilled off by passing in steam, the emulsion obtained is allowed to cool to room temperature while stirring, and the 6-chloro-2-benzylbenzothiazole of the formula

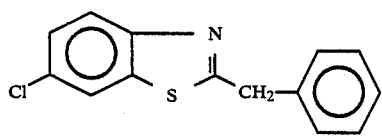

which separates out in the form of granules is isolated by filtration. Washing with water and drying in vacuo at 40° C.-60° C. give 121 parts of a product of melting point 79° C.-81° C.; this corresponds to a yield of 93.3% of theory, based on sodium salt employed.

The compound is pure according to chromatography, and is found by potentiometric titration with perchloric acid to have a purity of 98.2%.

EXAMPLES 23-27

If, in Example 22, the phenylacetyl chloride is replaced by aliquot amounts of an acyl chloride of the formula (10) and the sodium salt of 4-chloro-2-mercaptophenylurea is replaced by appropriate amounts of a sodium salt of the formula (11) and the procedure is otherwise carried out in the manner stated, the 2-substituted benzothiazoles of the formula (12) which are listed in Table 3 below are obtained, these benzothiazoles having the stated melting points, yields and purities:

TABLE 3

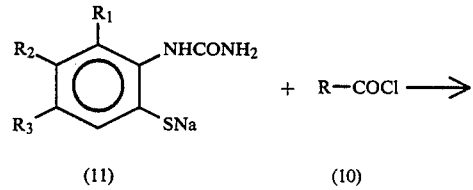

(11)      (10)

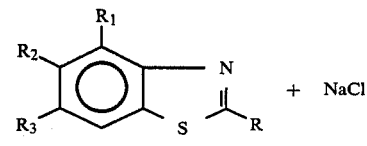

(12)

| Ex- am- ple | Educts (10/11) | | | | Product (12) | | |
|---|---|---|---|---|---|---|---|
| | R | $R_1$ | $R_2$ | $R_3$ | M.p. °C. | Yield | P |
| 23 | $CH_3$ | H | H | Br | 86–87° | 94,3% | 98,8% |
| 24 | $CH_3$ | H | $NO_2$ | H | 136–138° | 91,0% | 97,5% |
| 25 | $C_2H_5$ | H | Cl | H | 55–57° | 89,5% | 97,2% |
| 26 | 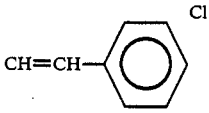 | Cl | H | Cl | 152–154° | 92,8% | 97,5% |

TABLE 3-continued

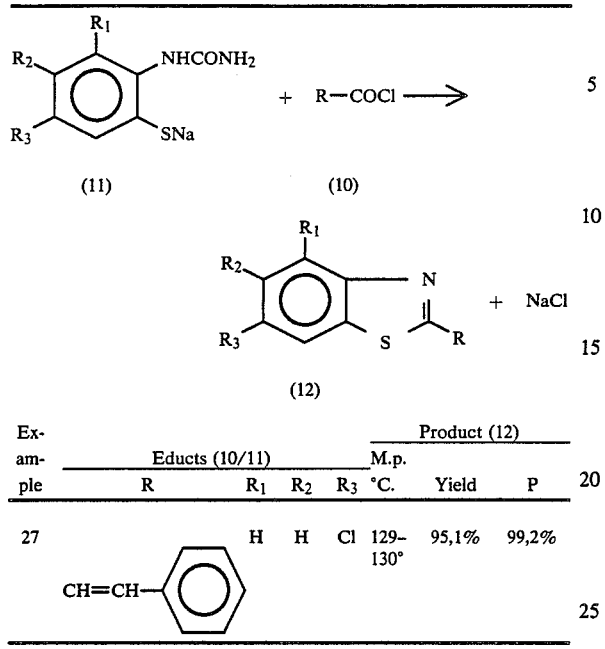

| Example | Educts (10/11) R | R₁ | R₂ | R₃ | Product (12) M.p. °C. | Yield | P |
|---|---|---|---|---|---|---|---|
| 27 | CH=CH—C₆H₅ | H | H | Cl | 129–130° | 95,1% | 99,2% |

EXAMPLE 28

85 parts of the sodium salt of 2-mercaptophenylurea (prepared according to Example 1 of European Pat. No. 0,039,483, by reacting 2-aminobenzothiazole with sodium hydroxide in ethylene glycol at 140° C., then filtering the reaction mixture and drying the resulting filter cake in vacuo at 100° C. until the weight remains constant) are suspended in 250 parts of o-chlorotoluene. 77 parts of benzoyl chloride are added dropwise in the course of 30 minutes at 90° C.-100° C., while stirring, and the mixture is heated to the boil and refluxed for 5 hours. Thereafter, the o-chlorotoluene is distilled off with steam, the resulting aqueous emulsion or suspension is cooled to room temperature and the precipitated 2-phenylbenzothiazole of the formula

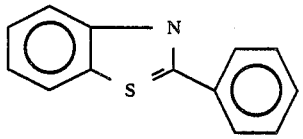

is isolated by filtration. Washing neutral with water and drying at 80° C. in a through-circulation oven give 100 parts of a product of melting point 110° C.-112° C.; this corresponds to a yield of 94.8% of theory, based on sodium salt employed.

The product is pure according to chromatography. Its purity determined by potentiometric titration (HClO₄ in glacial acetic acid) is 98.5%.

EXAMPLES 29–35

If, in Example 28, the benzoyl chloride is replaced by aliquot amounts of a substituted benzoyl chloride of the formula (13) and the procedure is otherwise carried out in the stated manner, the 2-phenylbenzothiazoles of the formula (14) which are substituted in the phenyl radical are obtained with the melting points, yields and purities listed in Table 4 below:

TABLE 4

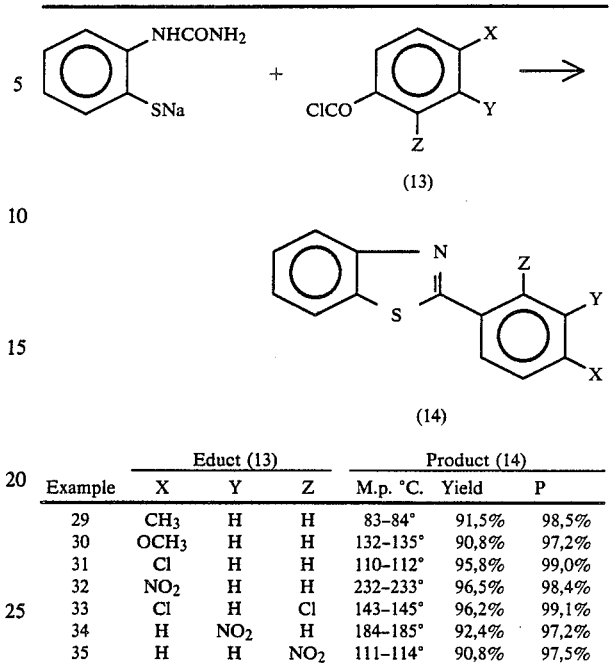

| Example | Educt (13) X | Y | Z | Product (14) M.p. °C. | Yield | P |
|---|---|---|---|---|---|---|
| 29 | CH₃ | H | H | 83–84° | 91,5% | 98,5% |
| 30 | OCH₃ | H | H | 132–135° | 90,8% | 97,2% |
| 31 | Cl | H | H | 110–112° | 95,8% | 99,0% |
| 32 | NO₂ | H | H | 232–233° | 96,5% | 98,4% |
| 33 | Cl | H | Cl | 143–145° | 96,2% | 99,1% |
| 34 | H | NO₂ | H | 184–185° | 92,4% | 97,2% |
| 35 | H | H | NO₂ | 111–114° | 90,8% | 97,5% |

EXAMPLES 36–42

If, in Example 28, the sodium salt of o-mercaptophenylurea is replaced by aliquot amounts of the sodium salt of a substituted o-mercaptophenylurea of the formula (15) (can be prepared, for example, analogously to Example 6 of European Pat. No. 0,039,483) and the procedure is otherwise carried out in the stated manner, 2-phenylbenzothiazoles of the formula (16) which are substituted in the benzene nucleus are obtained with the melting points, yields and purities listed in Table 5 below:

TABLE 5

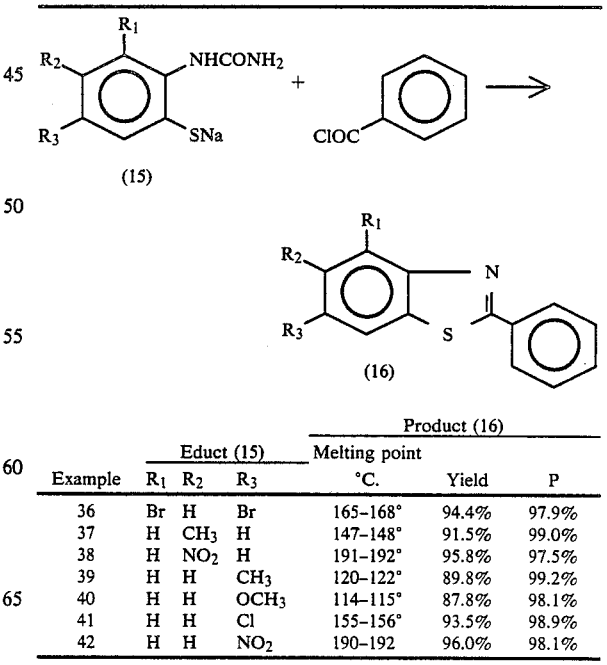

| Example | Educt (15) R₁ | R₂ | R₃ | Product (16) Melting point °C. | Yield | P |
|---|---|---|---|---|---|---|
| 36 | Br | H | Br | 165–168° | 94.4% | 97.9% |
| 37 | H | CH₃ | H | 147–148° | 91.5% | 99.0% |
| 38 | H | NO₂ | H | 191–192° | 95.8% | 97.5% |
| 39 | H | H | CH₃ | 120–122° | 89.8% | 99.2% |
| 40 | H | H | OCH₃ | 114–115° | 87.8% | 98.1% |
| 41 | H | H | Cl | 155–156° | 93.5% | 98.9% |
| 42 | H | H | NO₂ | 190–192 | 96.0% | 98.1% |

EXAMPLES 43-49

If, in Example 28, the sodium salt of o-mercaptophenylurea is replaced by aliquot amounts of sodium salt of a substituted o-mercaptophenylurea of the formula (17) (can be prepared, for example, analogously to Example 6 of European Pat. No. 0,039,483) and the benzoyl chloride is replaced by appropriate amounts of a substituted benzoyl chloride of the formula (13), and the procedure is otherwise carried out in the stated manner, the 2-phenylbenzothiazoles of the formula (18) which are substituted in the benzene and phenyl nucleus and are listed in Table 6 below are obtained, these compounds having the stated melting points, yields and purities:

TABLE 6

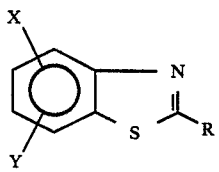

| | Educt (17) | | | | Educt (13) | | | Product (18) | | |
|---|---|---|---|---|---|---|---|---|---|---|
| Example | $R_1$ | $R_2$ | $R_3$ | $R_4$ | X | Y | Z | Melting point °C. | Yield | P |
| 43 | $CH_3$ | H | $CH_3$ | H | H | $CH_3$ | H | 71-74° | 85.2% | 96.8% |
| 44 | H | $CH_3$ | H | H | H | $NO_2$ | H | 184-185° | 96.5% | 99.1% |
| 45 | H | Cl | H | H | H | H | $NO_2$ | 195-197° | 96.8% | 98.9% |
| 46 | H | H | $CH_3$ | H | $OC_2H_5$ | H | H | 167-169° | 87.8% | 96.2% |
| 47 | H | H | Br | H | Br | H | H | 215-218° | 97.4% | 98.0% |
| 48 | H | H | $NO_2$ | H | $NO_2$ | H | H | 238-240° | 97.5% | 97.5% |
| 49 | H | H | H | $CH_3$ | H | $NO_2$ | H | 179-180° | 91.4% | 97.2% |

I claim:

1. A process for the preparation of a benzothiazole of the formula (1)

in which R denotes a $C_1$ to $C_6$-alkyl or $C_2$ to $C_6$-alkenyl group which is unsubstituted or substituted by a $C_1$ to $C_4$-alkoxy, an organic acyl group, phenyl, chlorophenyl, bromophenyl, alkylphenyl, a $C_1$ to $C_4$-alkoxyphenyl or nitrophenyl group or a halogen atom, or denotes a phenyl group which is unsubstituted or substituted by $C_1$ to $C_4$-alkyl, $C_1$ to $C_4$ alkoxy, carboxyl, —COO—($C_1$ to $C_4$)-alkyl, a cyano or nitro group or by a halogen atom, and X and Y each denote a hydrogen or halogen atom or a $C_1$ to $C_4$ alkyl. $C_1$ to $C_4$-alkoxy or nitro group, or together denote a fused benzene ring, wherein a salt of a corresponding 2-mercaptophenylurea of the formula (5),

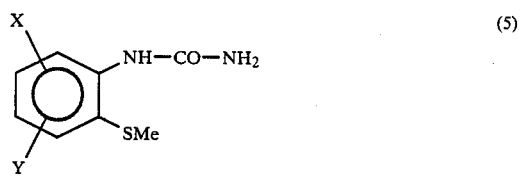

in which X and Y have the stated meanings and Me denotes an alkali metal atom or the equivalent amount of an alkaline earth metal atom is treated with an acylating agent of the formula (3)

$$R-CO-Z \qquad (3)$$

in which R has the above-mentioned meaning and Z represents OH, a halogen atom or the group $$-O-\underset{\underset{O}{\|}}{C}-R,$$

wherein R has the stated meaning, or with diketene, at a temperature from 0° C. to 200° C.

2. A process according to claim 1, wherein said organic acyl group is acetyl or benzoyl.

3. A process according to claim 1, wherein said 2-mercaptophenylurea of the formula (5) is obtained by reacting the corresponding 2-aminobenzothiazole of the formula (4)

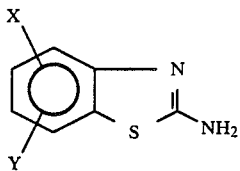

(4)

in which X and Y are as defined in claim 1, with an alkali metal or alkaline earth metal hydroxide in a ring-opening reaction mixture, the said 2-mercapto- phenylurea of the formula (5) being formed in said ring-opening reaction mixture.

4. A process according to claim 3, wherein the said 2-mercaptophenylurea of the formula (5), formed in said ring-opening reaction mixture, is isolated from said ring-opening reaction mixture for treatment with said acylating agent of the formula (3) or with diketene.

5. A process according to claim 3, wherein the said 2-mercaptophenylthiourea of the formula (5) is formed and suspended in said ring-opening reaction mixture and is not isolated from said ring-opening reaction mixture but is treated with said acylating agent of the formula (3) or with diketene while in suspension in said ring-opening reaction mixture.

* * * * *